(12) United States Patent
Haworth

(10) Patent No.: US 10,492,902 B1
(45) Date of Patent: Dec. 3, 2019

(54) MAMMARY PAPILLA IMPLANT AND SURGICAL METHOD

(71) Applicant: Steve A. Haworth, Gilbert, AZ (US)

(72) Inventor: Steve A. Haworth, Gilbert, AZ (US)

(*) Notice: Subject to any disclaimer, the term of this patent is extended or adjusted under 35 U.S.C. 154(b) by 49 days.

(21) Appl. No.: 16/027,355

(22) Filed: Jul. 4, 2018

(51) Int. Cl.
*A61F 2/12* (2006.01)

(52) U.S. Cl.
CPC ........ *A61F 2/12* (2013.01); *A61F 2220/0008* (2013.01); *A61F 2230/0006* (2013.01); *A61F 2230/0008* (2013.01); *A61F 2230/0019* (2013.01); *A61F 2230/0069* (2013.01)

(58) Field of Classification Search
CPC ......... A61F 2/12; A61F 2/52; A61F 2002/526
See application file for complete search history.

(56) References Cited

U.S. PATENT DOCUMENTS

| | | | |
|---|---|---|---|
| 4,217,889 | A | 8/1980 | Radovan et al. |
| 4,643,733 | A | 2/1987 | Becker |
| 6,755,861 | B2 | 6/2004 | Nakao |
| 8,529,624 | B2 | 9/2013 | Linares |
| 2012/0101575 | A1 | 4/2012 | Horne et al. |
| 2012/0143330 | A1 | 6/2012 | Linares |

FOREIGN PATENT DOCUMENTS

WO  WO-2015177796 A1 * 11/2015

OTHER PUBLICATIONS store_stevehaworth_com.pdf (website) by Steve Haworth, viewed on Jul. 4, 2018.
Gen_Beads_Bead_Strings_Spines—Steve_Haworth_Modified LLC. pdf.
Genital_Beading.pdf.
Genital_Beading-BME Encyclopedia.pdf.
Half_Cut_Beads—Steve_Haworth_Modified_LLC.pdf.
Horns—SteveHaworthModifiedLLC.pdf.
Pearling_body_modification-Wikipedia.pdf.
Steve_Haworth_steve_haworth_Instagram.pdf.
stevehaworth.com.pdf.
Tattoo_Artist_Invents_Prosthetic_Nipple_for_Breast_Cancer_Survivors_News Blog.pdf.
Welton_weltonecro_Instagram_photos_and_videos.pdf.pdf.

* cited by examiner

*Primary Examiner* — Thomas Sweet
*Assistant Examiner* — Rebecca Lynee Zimmerman
(74) *Attorney, Agent, or Firm* — Mark V. Loen

(57) ABSTRACT

The embodied invention is a nipple implant made from silicon and designed to be well anchored in position by attaching it to the skin of the patient. The implant includes support arms suitable for attachment to the underside of the dermis skin layer using sutures. An outer ring provides stability to the attaching arms and adds additional surfaces that will be surrounded by scar tissue to provide additional location stability.

Figure 1:
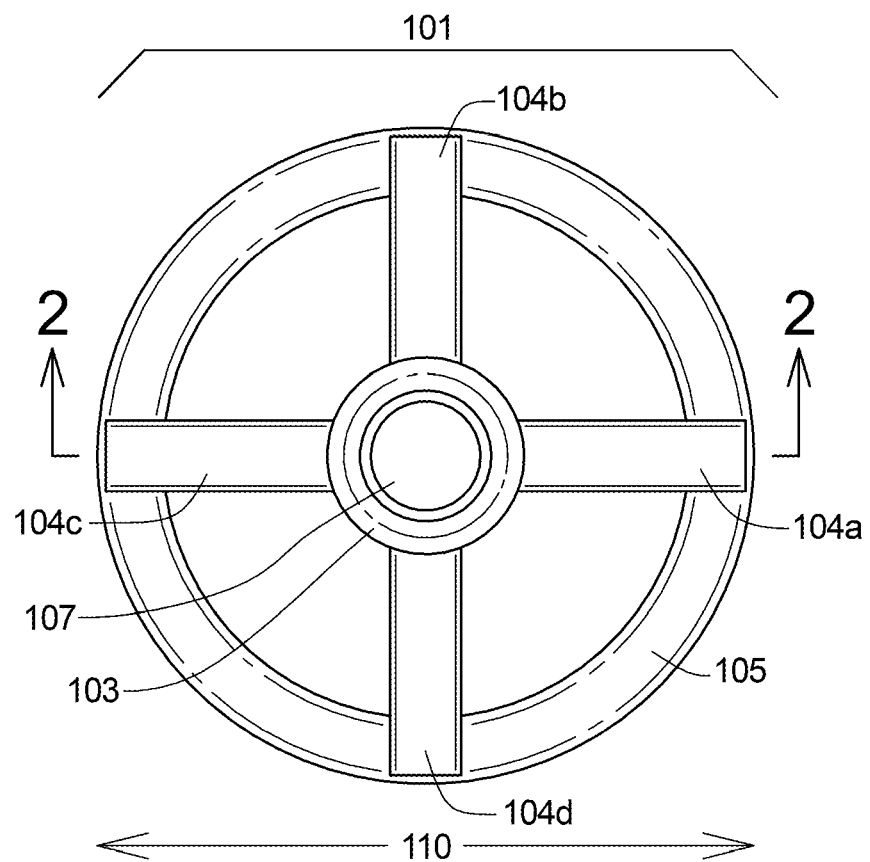

The nipple implant includes a center receptacle that secures a skin elevating plug that provides a skin protrusion. The plug is replaceable with an additional surgery to provide a gradual increase in the skin protrusion over a period of months. The area around the implant is tattooed to provide visual coloring that matches the natural areola shape and color.

7 Claims, 5 Drawing Sheets

MAMMARY PAPILLA IMPLANT AND SURGICAL METHOD

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING, A TABLE, OR COMPUTER PROGRAM LISTING

Not applicable.

BACKGROUND OF THE INVENTION

(1) Field of the Invention

This invention is directed to mammary prostheses and implants, that are related to reconstruction surgery after significant removal of the breast tissue.

The embodied invention specifically relates to breast nipple implants, which are useful after breast removal typically associated with mastectomy procedures. The disclosed invention describes an implant apparatus and method of inserting the implant, which is designed for improved appearance of the chest by providing a protruding nipple and areola appearance.

(2) Description of Related Art

Others have worked in the field of nipple prostheses and implants. U.S. Pat. No. 8,529,624 describes a breast implant as well as a nipple implant that is used after re-construction surgery. The nipple prostheses is inserted below the skin with two chambers for a fluid transfer from a reservoir and an extension chamber. However, there is no disclosure as to anchoring the nipple prostheses which is likely to become mobile under the skin due to the abundance of fatty tissue which will allow the prothesis to slide or retreat into the body. There are similar problems with U.S. Pat. No. 6,755,861, US 20120101575, and U.S. Pat. No. 9,308,081. These disclosures fail to recognize or address this problem.

Currently, in a commercial sense, a medical implant that provides a protruding nipple after a mastectomy is not known to be available. Although breast implants are widely available, some women feel incomplete after reconstructive surgery without a solution that provides a completely restored visual appearance.

Also, there is need in the art for an implant that is designed to be successfully placed under differing skin tightness. If the skin is too tight, inserting an implant with a high protruding surface under the skin will lead to skin thinning and skin damage, and increased likelihood of an infection and or rejection.

BRIEF SUMMARY OF THE INVENTION

The embodied invention discloses a nipple implant made from silicon and designed to be well anchored in position by attaching it to the dermis layer of the patient. The implant includes support arms suitable for attachment to the underside of the dermis skin layer using sutures. An outer ring provides stability to the attaching arms and adds additional surfaces that will be surrounded by scar tissue to provide additional location stability.

The nipple implant includes a center receptacle that secures a skin elevating plug that provides a skin protrusion. The plug is replaceable with an additional surgery to provide a gradual increase in the skin protrusion over a period of months. The area around the implant is preferably tattooed to provide visual coloring that matches the natural areola shape and color.

The nipple implant is installed by minor surgery where a small quarter round cut is made in the skin tissue at the desired location. Elevating tools are inserted into the cut to separate the lower dermis skin layer from the subcutis layer to create a pocket for the implant. The implant is then folded, inserted into the pocket, allowed to unfold, and manually positioned. Sutures are looped through the epidermis and dermis skin layers, around the support arms, and then back through the epidermis and dermis skin layers. Additional sutures are used to close the cut.

BRIEF DESCRIPTION OF THE SEVERAL VIEWS OF THE DRAWING(S)

Figure 2:
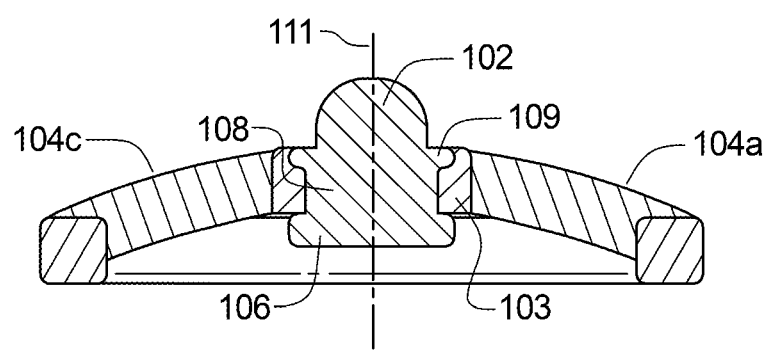
Figure 3:
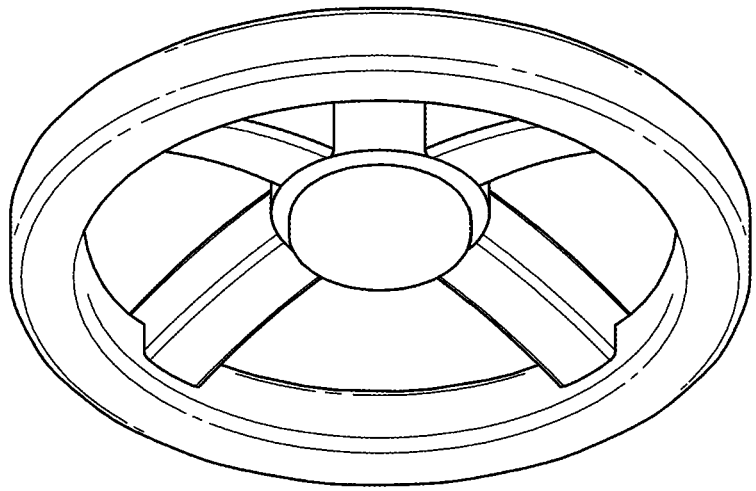
Figure 4:
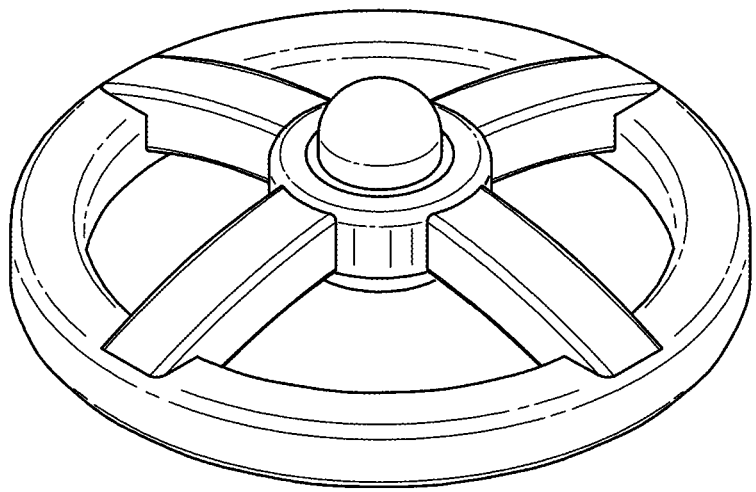
Figure 5A:
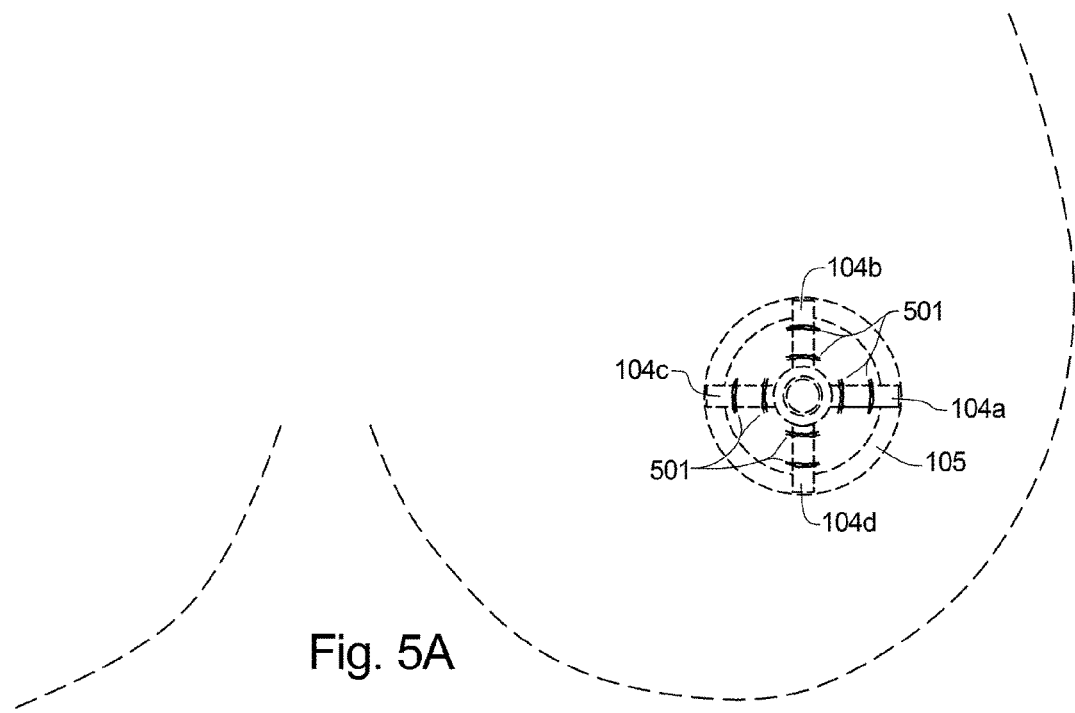
Figure 5B:
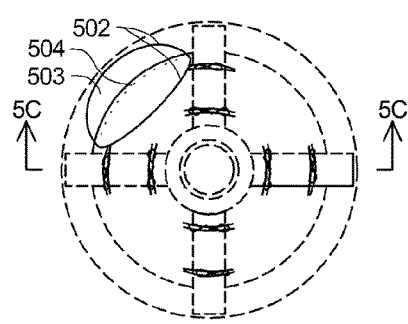
Figure 5C:
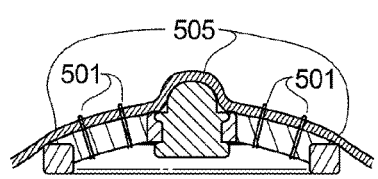
Figure 6:
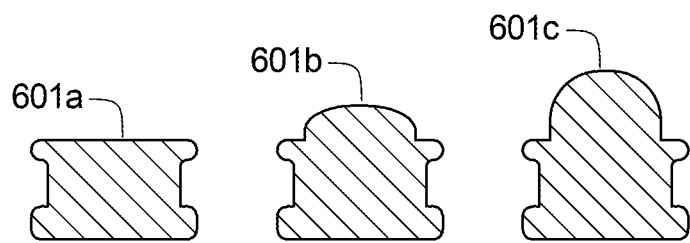
Figure 7:
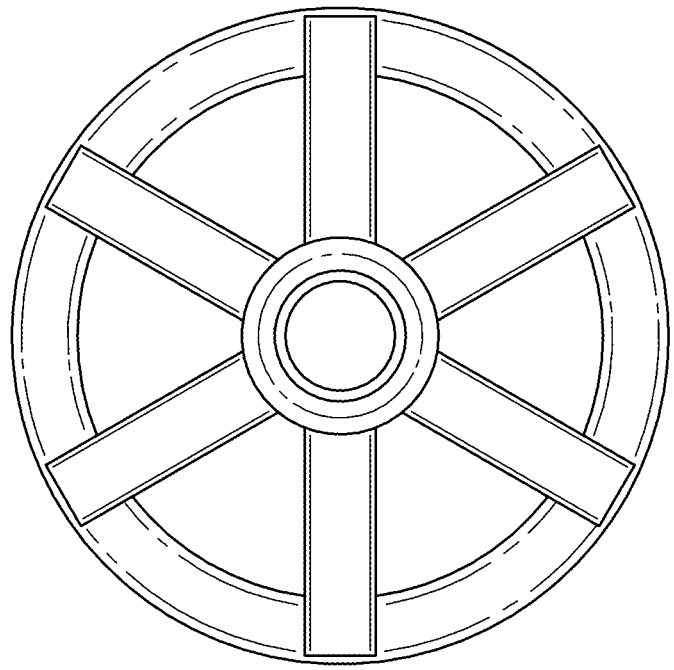
Figure 8:
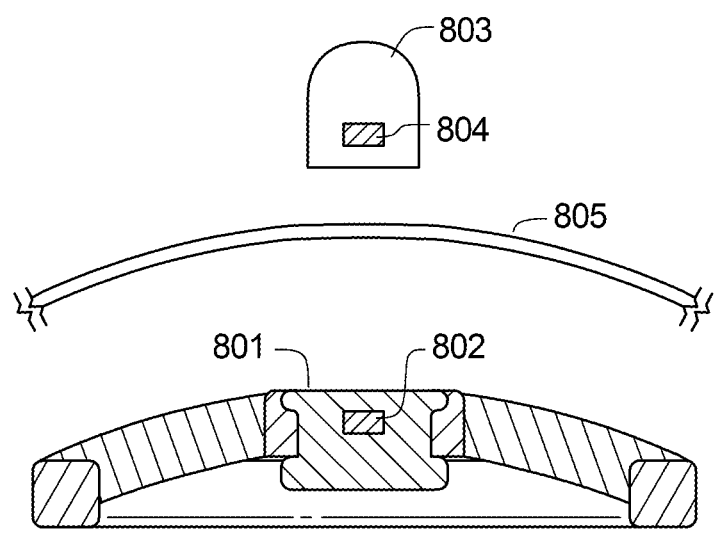
Figure 9:
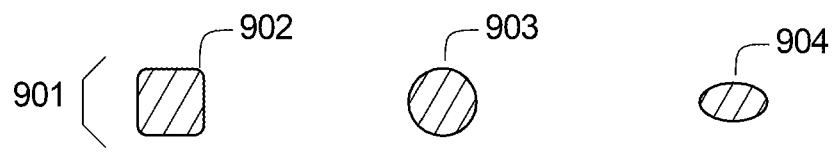

FIG. 1 shows a top view of the mammary papilla implant.
FIG. 2 is a cross section of FIG. 1.
FIG. 3 is an upper isometric view of the implant.
FIG. 4 is a lower isometric view of the implant.
FIGS. 5A-5C illustrate how the implant is anchored with sutures.
FIG. 6 illustrates how a skin elevating plug can be adapted for a tight skin.
FIG. 7 illustrates an alternate embodiment of the implant with a different arm support structure.
FIG. 8 illustrates how an external prosthetic nipple is attached to an implant by a magnet.
FIG. 9 illustrates implant cross sections that avoid sharp corners.

DETAILED DESCRIPTION OF THE INVENTION

FIG. 1 shows a top view of the embodied mammary papilla implant 101. It includes a skin elevating plug 107 and a plug receptacle 103. An outer ring 105 provides support and connection for four support arms 104a-d. The entire implant is made from medical grade silicon to ensure resistance to a rejection by the surrounding tissue. Additionally, it is flexible for improved insertion underneath the skin with a minimum surgical opening in the skin.

FIG. 2 shows a cross section through the middle of FIG. 1 for better clarity as to the construction of the implant 101. The skin elevating plug 107 is made up of a raised dome 102, an upper insertion ring 109, a narrow ring 108 and a lower lock ring 106. The plug receptacle 103 is shaped similarly to the upper insertion ring and narrow ring, but at a slightly larger diameter (relative to the plug) to create a pressure fit. The overall outside diameter 110 of the implant is between 1 to 2 inches. The implant has a center axis 111 that is perpendicular to plane of the outer ring.

The skin elevating plug 107 is not permanently attached to the plug receptacle. The plug can be pulled out and replaced with a different skin elevating plug that has a higher (or lower) raised dome. See FIG. 6. The ability to utilize differing dome heights is an important feature of the disclosed invention. The fit between the center receptacle and the skin elevating plug is an interference fit so that the plug is held in place by pressure.

The skin elevating plug 107 is designed to be re-inserted into the plug receptacle in the case of a car accident where the plug is pushed out of the plug receptacle. A surgeon would normally be able to manipulate the elevating plug back into position and lock it in place without a surgical incision.

FIG. 3 is an upper isometric view of the preferred implant embodiment. FIG. 4 is a lower isometric view of the implant.

FIG. 5A shows the implant when located at a desired position. The implant is illustrated in FIG. 5A in dashed lines as it is below the skin. FIG. 5B shows a closer view of the implant after being inserted below the skin through a surgical opening. FIG. 5C shows a cross section of FIG. 5B. The implant is anchored to the skin 505 by sutures 501 that loop through the skin and around the implant support arms 104*a-d*.

In FIG. 5B, a quarter round surgical cut 504 (dotted line) is made through the skin exposing part of the outer ring 503 of the nipple implant. The skin is pulled back as shown by the skin edges 502 in a rough shape of a football.

FIG. 6 shows three different profiles of the skin elevating plug. A flat profile plug 601*a* is used when the surgeon judges that the skin will be tight when the implant is inserted, and the skin may not immediately accept a protruding profile. A moderately raised profile 601*b* is used when the surgeon judges that the skin will accept a moderate profile. A final profile 601*c* is used when the skin is not tight and will readily accept a final profile. With additional surgeries, the skin elevating plug can be replaced to increase the protrusion when additional stretching is possible.

After a complete mastectomy, the areola may have been removed, and in this case an areola is tattooed on the exterior skin surface. The tattoo preferably includes coloring that matches a typical areola color of the patient. The scar tissue on the skin from the sutures and radial insertion cut, enhance the visual appearance of the new areola by providing texture.

Also, to improve the appearance, the skin protrusion is preferably tattooed to create a natural nipple color and appearance.

To insert the implant, a small incision is made through the epidermis and dermis skin layers. Then a subcutaneous elevator used to create the pocket area for the implant between the dermis and subcutis (fatty tissue) layers. Once the implant cavity is formed, the implant is inserted into the cavity and manually adjusted in place through surgical tools and outside manipulation.

A minimum surgical opening for the implant is important to improve post operative healing. Preferably, the radial insertion cut for the implant is ¼ of a circle or less, and the implant is folded/rolled to a small profile for insertion. The implant is folded/rolled to fit through the opening and allowed to unfold/unroll once inside the implant cavity. The cut is preferably an arc of a circle with the center of the circle located where center of the implant will be located. By making the entry cut in this manner, the scar tissue will enhance and blend in with the areola appearance. As little as a¹/a" entry skin opening is needed for a for 1⅓" diameter implant.

In a preferred embodiment, as illustrated in FIG. 5, sutures 501 anchor the support arms 104*a-d* to the inside dermis layer. As illustrated, two sutures per support arm are used to anchor the implant to the inside dermis layer. Optionally, three sutures per support arm are used. This provides reasonable spacing for the sutures to anchor the implant and allow better post operative healing. Optionally, the outer ring is also sutured to the dermis skin layer.

It is important that the surgical opening does not cut any muscle or any membrane. Unneeded cuts increase the likelihood of infection and prolonged healing.

An elevating tool is used to create the implant pocket. Surgical elevating tools are known in the art.

Post-operative issues that may arise include infection and rash, similar as other implants.

Typically, 2 to 4 weeks of healing are needed before the sutures can be removed. Circumferential suture orientation (as illustrated in FIG. 5) creates scaring that enhances the appearance and texture of an areola.

If the insert is not well anchored to the skin, there will be problems with the insert moving post operation. Without good anchoring, the natural pressure on the chest from clothing, bra, sleeping, etc. will cause the implant to sink into the fatty tissue (subcutis layer). If the implant sinks, then the desired protrusion will not be created. To anchor the implant to the skin, there is need for an implant to have a large enough size for it to become positionally stable. Additionally, when healing, scar tissue will be created which will aid in bonding the implant to the skin. To this end, the implant size is preferably 1 to 2 inches in the outermost diameter.

It is highly preferable that the implant utilizes rounded edges, or a rounded cross sectional profile. In particular, the support arms, the skin elevating plug, and the outer ring should have rounded edges. FIG. 9 illustrates a rectangular cross section 901 (including a square) with rounded edges 902. Also, an ellipse cross section 904 or a circle 903 cross section (generally described as a type of ellipse) has a rounded profile. Sharp edges will irritate the skin and allow un-needed chafing or skin damage from a higher localized pressure. The elliptical cross section is particularly useful when a lower outer ring profile is desired due to tight skin or less tissue to work with.

During the healing process, scar tissue will surround the implant and improve the bonding to the dermis layer. The scar tissue greatly aids in stabilizing the implant location.

It is expected that the majority of patients have skin that is loose enough to receive an implant with a protruding curve. However, a tight skin will require a multiple surgical approach to create the desired nipple protrusion. General surgical steps are:

1. Perform a first surgery to insert an implant with a flat center profile, suture it in place, and close up the incision.
2. Allow healing for approximately 2-3 months.
3. Perform a second surgery by making a second incision, pull out the plug with the flat center profile and put in a moderate profile skin elevating plug (approx. ³⁄₁₆" profile height). Close up the incision.
4. Allow healing for approximately 2-3 months.
5. Perform a third surgery by making a third incision, pull out the moderate profile skin elevating plug, and put in a final profile skin elevating plug (approx. ⅜" profile height). Close up the incision.
6. Allow healing for approximately 2-3 months.
7. Add tattooing to create an areola and color the nipple protrusion.

The end result is a nipple with a protrusion about ½" away from the body that is very natural looking.

This multistep process takes 6-9 months and three surgeries to complete when there is tight skin.

The skin elevating plug is made from silicone that is very flexible; so that it is not difficult to lift out of, or insert into, the center receptacle. By using this surgical multistep process, the protrusion can be completed in three steps that will avoid skin stretching complications when increasing the protrusion.

When a breast reconstruction is done, the nipple implant is inserted above the breast implant between the dermis and subcutis layers. The breast implant is typically inserted under the muscle, which is under the subcutis layer.

An alternate method of creating a nipple appearance when the skin is tight, is the use of an external prosthetic nipple as illustrated in FIG. 8. A prosthetic nipple 803 with a prosthetic magnet 804 attaches to an implant magnet 802 which is on the top of a flat profile plug 801. However, there is long term difficulty with this method as the skin 805 is compressed between the two magnets. A lighter magnet strength is better for skin circulation, but the prosthetic nipple is more likely to fall off.

While various embodiments of the present invention have been described, the invention may be modified and adapted to various operational methods to those skilled in the art. Therefore, this invention is not limited to the description and figure shown herein, and includes all such embodiments, changes, and modifications that are encompassed by the scope of the claims.

I claim:

1. A mammary nipple implant comprising:
   A. an outer ring further comprising:
      a. an outside diameter between 1 and 2 inches inclusive,
      b. a center axis perpendicular to the plane of said outer ring, and
      c. said outer ring having an elliptical cross section or a rectangular shaped cross section with rounded edges,
   B. a skin elevating plug further comprising:
      a. a dome,
      b. an insert ring,
      c. a narrow ring, and
      d. a locking ring,
   C. a plug receptacle aligned to said center axis further comprising:
      a. a cylindrically shaped exterior,
      b. an internal plug chamber aligned to said center axis, and
      c. said plug chamber having a radially symmetric internal plug profile,
   D. wherein said skin elevating plug is located in said plug chamber,
   E. wherein said internal plug profile secures said skin elevating plug,
   F. a plurality of elongated support arms further comprising:
      a. said support arms are radially oriented to said center axis,
      b. said support arms are connected to an inside diameter of said outer ring,
      c. said support arms are connected to said cylindrically shaped exterior of said plug receptacle, and
      d, said support arms having an elliptical cross section or a rectangular shaped cross section with rounded edges,
      and
   G. said outer ring, said skin elevating plug, said plug receptacle, and said support arms are made from a medical grade silicone.

2. A surgical method for installing a mammary nipple implant comprising:
   A. providing a nipple implant further comprising
      a. an outer ring further comprising:
         i. an outside diameter between 1 and 2 inches inclusive,
         ii. a center axis perpendicular to the plane of said outer ring, and
         iii. said outer ring having an elliptical cross section or a rectangular shaped cross section with rounded edges,
      b. a first skin elevating plug further comprising:
         i. a dome,
         ii. an insert ring,
         iii. a narrow ring, and
         iv. a locking ring,
      c. a plug receptacle aligned to said center axis further comprising:
         i. a cylindrically shaped exterior,
         ii. an internal plug chamber aligned to said center axis, and
         iii. said plug chamber having a radially symmetric internal plug profile,
      d. wherein said skin elevating plug is located in said plug chamber,
      e. wherein said internal plug profile secures said skin elevating plug,
      f. a plurality of elongated support arms further comprising:
         i. said support arms are radially oriented to said center axis,
         ii. said support arms are connected to said outer ring,
         iii. said support arms are connected to said plug receptacle, and
         iv. said support arms having an elliptical cross section or a rectangular shaped cross section with rounded edges,
         and
      g. said outer ring, said skin elevating plug, said plug receptacle, and said support arms are made from a medical grade silicone,
   B. making an incision in a patient's skin at a desired location,
   C. creating a cavity between a dermis skin layer and a subcutis layer at said desired location,
   D. placing said nipple implant in said cavity,
   E. anchoring said nipple implant by suturing said nipple implant to said dermis skin layer,
   F. closing said incision, and
   G. allowing time for said patient's skin at said desired location to heal.

3. The method according to claim 2, wherein an areola tattoo and a nipple tattoo is placed on said skin of said patient at said desired location.

4. The method according to claim 2 further comprising:
   A. making a second incision at said desired location,
   B. removing said first skin elevating plug,
   C. placing a second skin elevating plug in said plug receptacle,
   D. closing said second incision, and
   E. allowing said second incision to heal.

5. The method according to claim 4, wherein
   A. making a third incision at said desired location,
   B. removing said second skin elevating plug,
   C. placing a third skin elevating plug in said plug receptacle,
   D. closing said second incision, and
   E. allowing said third incision to heal.

6. The method according to claim 5, wherein an areola tattoo and a nipple tattoo is placed on said skin of said patient at said desired location.

7. A mammary nipple implant comprising:
- A. an outer ring further comprising:
  - a. an outside diameter between 1 and 2 inclusive,
  - b. a center axis perpendicular to the plane of said outer ring, and
  - c. said outer ring having an elliptical cross section or a rectangular shaped cross section with rounded edges,
- B. a skin elevating plug having a dome,
- C. a plug receptacle aligned to said center axis further comprising:
  - a. a cylindrically shaped exterior, and
  - b. an internal plug chamber aligned to said center axis,
- D. wherein said skin elevating plug is located in said plug chamber,
- E. wherein said plug receptacle secures said skin elevating plug,
- F. a plurality of elongated support arms further comprising:
  - a. said support arms are radially oriented to said center axis,
  - ii. said support arms are connected to said outer ring,
  - iii. said support arms are connected to said plug receptacle, and
  - iv. said support arms having an elliptical cross section or a rectangular shaped cross section with rounded edges,
  and
- G. said outer ring, said skin elevating plug, said plug receptacle, and said support arms are made from a medical grade silicone.

\* \* \* \* \*